US005300433A

United States Patent [19]

Hrinda et al.

[11] Patent Number: 5,300,433

[45] Date of Patent: Apr. 5, 1994

[54] METHODS FOR THE INACTIVATION OF VIRUSES IN VIRAL-CONTAMINATED PHARMACEUTICAL COMPOSITIONS

[75] Inventors: Michael E. Hrinda, Gwynedd Valley; Rose D'Alisa, Warrington; George C. Tarr, Jeffersonville, all of Pa.

[73] Assignee: Rhone-Poulenc Rorer Pharmaceuticals Inc., Collegeville, Pa.

[21] Appl. No.: 765,479

[22] Filed: Sep. 25, 1991

Related U.S. Application Data

[63] Continuation of Ser. No. 366,855, Jun. 15, 1989.

[51] Int. Cl.[5] .......................... C12N 7/06; C12N 7/04; A61K 35/14; C07K 15/04

[52] U.S. Cl. .................................... 435/238; 435/236; 514/21; 424/530; 424/94.3; 530/381; 530/384; 530/380

[58] Field of Search ................ 435/238, 236; 424/530, 424/85.4, 85.8, 86, 94.3; 530/381, 384, 387, 389, 413, 414; 514/21

[56] References Cited

U.S. PATENT DOCUMENTS 4,540,573 9/1985 Neurath et al. ..................... 530/381
4,673,733 6/1987 Chandra et al. .................... 530/413
4,732,683 3/1988 Georgiades et al. ................ 530/351

FOREIGN PATENT DOCUMENTS 8501941 5/1985 World Int. Prop. O. .......... 530/381

OTHER PUBLICATIONS

Almeida et al, J. Med. Vir., 4:269-277 (1979).
Limentani et al, Blood, vol. 70, No. 5 (Nov.), 1987 pp. 1312-1315.
Austen et al, Thromb Haemostas 48(1) 46-48 (1982).

*Primary Examiner*—Jacqueline Stone
*Attorney, Agent, or Firm*—Rosanne Goodman; Martin F. Savitzky

[57] ABSTRACT

The present invention provides a fail-safe combination of chemical and physical means for rendering a blood product which comprises a labile blood protein free of viruses without incurring protein denaturation. The blood product is contacted with an effective amount of a selected chemical disinfectant, preferably, sodium thiocyanate in combination with a physical process, preferably, ultrafiltration. The blood product may be plasma, serum, plasma concentrate, cryoprecipitate, cryosupernatant, plasma fractionation precipitate or plasma fractionation supernatant containing viruses such as hepatitis or human immunodeficiency virus.

11 Claims, No Drawings

METHODS FOR THE INACTIVATION OF VIRUSES IN VIRAL-CONTAMINATED PHARMACEUTICAL COMPOSITIONS

This is a continuation of co-pending application Ser. No. 07/366,855, filed on Jun. 15, 1989.

BACKGROUND OF THE INVENTION

1. Field of the Invention

This invention relates to methods for the inactivation of viruses in virus-contaminated pharmaceutical compositions containing proteinaceous components, such as coagulation factors, by the use of chemical inactivation and/or physical processes. In particular, this invention relates to blood plasma or other plasma protein-containing compositions which are to be rendered free of viral infectivity, such blood plasma or fractions thereof having valuable labile proteins, such as, for example Factor IX. .A specific method of the invention requires the use of sodium thiocyanate and ultrafiltration.

2. Description of Related Art

Blood is made up of solids (cells, i.e., erythrocytes, leukocytes, and thrombocytes) and liquid (plasma). The cells contain potentially valuable substances such as hemoglobin, and they can be induced to make other potentially valuable substances such as interferons, growth factors, and other biological response modifiers. The plasma is composed mainly of water, salts, lipids and proteins. Prior to the availability of a more detailed description of individual protein components, the proteins were divided into groups; initially as simply "albumins" and "globulins". Typical antibodies (immune serum globulins) found in human blood plasma include those directed against infectious hepatitis, influenza H, etc.

Whole blood must be carefully typed and cross matched prior to administration in blood transfusions. Plasma, however, does not generally require prior testing. For certain applications, only a proper fraction of the plasma is required, such as factor VIII complex for treatment of hemophilia or von Willebrand's disease. The rationale for use of specific fractions of blood is that blood contains a number of differently formed elements as well as various plasma proteins and constituents which have many functions. Thus, a single donation of a unit of whole blood can provide red blood cells, platelets, plasma, and cryoprecipitated factor VIII-fibrinogen concentrate. Pheresis procedures are able to supply large quantities of granulocytes, platelets, and plasma from single donors. The rationale for using blood components is that a patient usually requires replacement of only a specified component (See: Greenwalt et al: General Principles of Blood Transfusion, A.M.A. Editorial Board, 1978). Remaining components can be then used to treat patients who require other specific components, thereby allowing several patients to benefit from each blood unit donated, thereby maximizing the benefit realizable therefrom. The separation of blood into components and their subsequent fractionation allows the proteins to be concentrated. Of great importance, too, is the fact that the plasma fractions can be stored for much longer periods than whole blood and they can be distributed in liquid, frozen, or dried state. Finally, it allows, in some cases, salvaging from blood banks the plasma portions of outdated whole blood that are unsafe for administration as whole blood.

Proteins found in human plasma include prealbumin, retinol-binding protein, albumin, alpha-globulins, beta-globulins, the coagulation proteins (Factors II, VII, IX, X, V, VIII, XI, XII, XIII and inhibitors such as protein C, antithrombin III, etc.) fibronectin, immunoglobins (immunoglobulins G, A, M, D, and E), and the complement components. There are currently more than 100 plasma proteins that have been described. A comprehensive listing can be found in the "The Plasma Proteins", ed. Putnam, F. W., Academic Press, New York (1975)

Proteins found in the blood cell fraction include hemoglobin, fibronectin, fibrinogen, enzymes of carbohydrate and protein metabolism, etc. In addition the synthesis of other proteins can be induced, such as interferons and growth factors.

Plasma can be chemically fractionated to provide albumin or plasma protein fraction, Factor VIII concentrate, Factor IX complex and immune serum globulin.

Blood plasma fractionation generally involves the use of organic solvents such as ethanol, ether and polyethylene glycol at low temperatures and at controlled pH values to effect precipitation of a particular fraction containing one or more plasma proteins. The resultant supernatant can itself then be precipitated and so on until the desired degree of fractionation is attained. More recently, separations are based on chromatographic processes. A survey of blood fractionation appears in Kirk-Othmer's Encyclopedia of Chemical Technology, Third Edition, Interscience Publishers, Volume 4, pages 25 to 62.

The major components of a cold ethanolfractionation are as follows:

| Fraction | Proteins |
|---|---|
| I | fibrinogen; cold insoluble globulin; Factor VIII; properdin |
| II and III | IgG; IgM; IgA; fibrinogen; beta-lipoprotein; prothrombin; plasminogen; plasmin inhibitor; Factor V; Factor VII; Factor IX; Factor X; thrombin; antithrombin; isoagglutinins; ceruloplasmin; complement C'1, C'3 |
| IV-1 | alpha-1-lipoprotein, ceruloplasmin, plasmin-inhibitor; Factor IX; peptidase; alpha-and-beta-globulins |
| IV-4 | transferrin; thyroxine binding globulin; serum esterase; alpha-1-lipoprotein; albumin; alkaline phosphatase |
| V | albumin; alpha-globulin |
| VI | alpha-1-acid glycoprotein; albumin |

The above fractionation scheme can serve as a basis for further fractionations. Fraction II and III, for example, can be further fractionated to obtain immune serum globulin (ISG), a mixture primarly of Igb antibodies.

Another fractionation scheme involves use of frozen plasma which is thawed into a cryoprecipitate containing AHF (antihemophilic factor) and fibronectin and a cryosupernatant. The cryoprecipitate is then fractionated into fibronectin and AHF.

Polyethylene glycol is among the agents which have been used to prepare high purity AHF and non-aggregated ISG.

In the development of new products from human plasma, at least three major problems are always present. These are contamination with pyrogens (endotoxins), transmission of viral hepatitis or other viral diseases, and activation of the coagulation enzymes.

Solutions of pharmaceutical compositions which are intended to be parenterally administered in man (or in veterinary applications) are required to be sterilized from infective microorganism such as bacteria and fungi. A common method is to subject the composition to steam sterilization (autoclaving) at temperatures in excess of 100° C. at hyperbaric pressures for a time sufficient to be efficacious. This treatment kills viruses but can be deleterious or destructive to certain heat-sensitive compositions such as those which contain proteinaceous components such as coagulation Factors VIII, IX, II, VII, X, and the like.

Pyrogens are lipopolysaccharides (LPS) derived from the outer cell wall of gram-negative bacteria. They are toxic materials which are also known as endotoxins to distinguish them from toxic substances synthesized and excreted by the intact bacterium. Pyrogens have numerous biologic activities which include the production of fever, activation of clotting mechanisms and induction of shock. Consequently, in addition to the need for sterility from infectious agents, it is essential that pyrogenic substances be removed and that the causative bacteria be rendered innocuous by sterilization or other such treatment of the final plasma product.

Blood coagulation factors play a vital role in the normal coagulation mechanism. For instance, patients with a deficiency of Factor IX exhibit severe bleeding problems ("Hemophilia B"). It would be desirable to be able to isolate substantial quantities of Factor IX and other vitamin K-dependent proteins for therapeutic administration, as well as for scientific study.

Factor IX complex is a lyophilized pooled plasma derivative rich in Factors IV, VII, IX and X. It is an alternative to plasma therapy. It supplies vitamin K-dependent clotting factors in a much smaller volume than plasma but with a significantly higher hepatitis risk.

Factor IX containing concentrates are a unique and highly valuable blood product which are life-saving when used to control bleeding in patients suffering with Factor IX deficiency (Hemophilia B). These products have also been used to treat those patients afflicted with Hemophilia A having inhibitors, although clinical verification of this application is still in progress. Factor IX containing concentrates are also used to arrest serious hemorrhages or to avert operative and post operative bleeding in patients with other congenital clotting factor deficiencies and for multiple factor deficiency induced by an overdose of warfarin-type drugs, i.e., oral anticoagulants.

Commercial concentrates of Factor IX have been previously prepared using ion exchange resins to bind vitamin K-dependent clotting factors and separate these proteins from the bulk of other plasma proteins. These clotting factor concentrates are then eluted from the resin and vialed for therapeutic use without further purification. Such concentrates tend to have thrombogenic potential probably because they contain extraneous vitamin K-dependent clotting factors and/or phospholipid. Further, such concentrates have been a suspected vehicle in the transmission of viral diseases including hepatitis and acquired immune deficiency syndrome ("AIDS"). Further, crude concentrates of Factor IX are not stable for long periods in solution and therefore cannot be used for constant infusion therapy which limits their value in chronic replacement therapy.

Recent efforts to create Factor IX using a recombinant DNA approach have been frustrated by the difficulty encountered in separating Factor IX from culture supernatants with currently accepted techniques. (See: Anson DS, Austen DEG, and Brownless GG. "Expression of active human clotting Factor IX from recombinant DNA clones in mammalian cells." Nature 1985; 315:683-685; de la Salle H. Altenburger W. Elkaim R., Dott K., et al. "Active gamma-carboxylated human Factor IX expressed using recombinant DNA techniques." Nature 1985; 316:268-270; and Busby S., Kumar A., Joseph M., Halfpap L. Insley M. et al. "Expression of active human Factor IX in transfected cells." Nature 1985; 316:271-273). Thus, there remains a medical need for a safe preparation of Factor IX obtained from human plasma.

Numerous attempts have been made to inactivate viruses such as lipid-containing viruses of hepatitis B virus (HBV) and human immunodeficiency virus (HIV) in mammalian, especially, human, blood plasma. It is the practice in some countries to effect inactivation of the hepatitis B virus in the blood plasma by contacting the plasma with a viral inactivating agent of the type which crosslinks with the proteinaceous protein of hepatitis B virus or which interacts with the nucleic acid of the virus. For instance, it is known to attempt to inactivate hepatitis B virus by contact with an aldehyde (such as formaldehyde) whereby crosslinking to the protein is effected and the hepatitis B virus is inactivated. It is also known to effect inactivation of the virus by contact with beta-propiolactone (BPL), an agent which acts on the nucleic acid as well as protein components of the virus. It is further known to use ultraviolet (UV) light, especially after a beta-propiolactone treatment. It is believed that these methods are not suitable for the inactivation of the virus in plasma due to the observation that most of these inactivating agents (formaldehyde, beta-propiolactone and sodium hypochlorite) denatured or altered the valuable proteinaceous components of the plasma, especially so-called "labile" blood coagulation factors of the plasma.

The removal of bacteria and fungi from such heat-sensitive proteinaceous compositions is generally accomplished by the use of a bacterially retentive filter. Typical examples are the membrane filters in the porosity range 0.1-0.2 microns (100-200 nanometers) produced by Pall Corporation and Millipore Corporation. Generally, the proteinaceous components in the pharmaceutical composition remain undamaged. However, it is known that membrane filters can fail to retain highly infectious and dangerous microorganisms such as virus particles. Filter devices can be designed to retain some virus particles if the effective filter porosity is of a small enough size. Such devices have sometimes been used to harvest viral particles, e.g., during the manufacture of viral vaccines. Most viral particles, however, are smaller in size than the effective porosity of the membrane filter and are not retained. For example, the hepatitis B virus, which may be present in coagulation factor solutions made from human plasma, has a diameter of 42 nanometers (nm) and will readily pass through a 100 nm (0.1 micron) membrane filter.

It is well-known that plasma and products made from plasma may transmit hepatitis. Initially, interest in viral transmission focused primarily on hepatitis B antigen ($HB_sA_g$) as an indicator of the presence of the offending agent (hepatitis B virus) and attempts at eliminating this agent have led to widespread screening of all plasma used in transfusion by commercially available and approved laboratory procedures. While such laboratory screening has apparently decreased the incidence of hepatitis B in patients receiving whole blood transfusions, there has not been significant improvement in the incidence of the disease transmitted from plasma products Chronic users of blood products are at risk from the disease unless maintained in an immune state by innoculation with a vaccine. While effective, this may have other clinical risks associated with it. Attempts to remove the virus by various adsorption procedures or precipitation techniques, e.g. with polyethylene glycol, have not proven to fully eliminate infectivity. There is some evidence that the combination of ultraviolet light and B-propionolactone may be helpful in inactivating the virus in certain plasma products. However, there is some apprehension the B-propionolactone has carcinogenic properties.

In order to increase the safety of pharmaceutical compositions which contain heat-sensitive proteinaceous components and which may contain dangerous virus particles, additional processing is required. This processing includes heating solutions of the proteinaceous components with special stabilizers to protect biologic potency, heating lyophilized preparations of the proteinaceous components, and treating solutions of proteinaceous components with organic solvents and other virucidal agents. Most of these methods are burdensome, time consuming, or destructive of the protein due to the rigorousness of the treatment. There are still questions about the efficacy of any one of these procedures applied singly to plasma products.

While the development of screening tests for hepatitis B has been of limited value in reducing transmission of the disease, the identification of this virus (as well as the hepatitis A virus) has led to the recognition of a third virus which is apparently responsible for the majority of cases of hepatitis transmitted by blood plasma derivatives. This virus is referred to as "non-A, non-B hepatitis".

Methods for the inactivation of hepatitis B virus in the plasma are known but are usually impractical. One method involves the addition of antibodies to the plasma whereby an immune complex is formed. The expense of antibody formation and purification add significantly to the cost of the plasma production; furthermore, there is no assurance that a sufficient quantity of non-A, non-B virus is inactivated since the method is specific for the hepatitis B virus. There is currently no approved and available test for non-A, non-B antibodies or virus, though there are reports of progress in achieving this; hence, it is not as yet possible to select plasma containing high titers of anti non-A, non-B antibody, nor indicate that this approach would be practicable.

As progress has been made in the development of human plasma derived therapeutics, the necessity of viral sterilization has become manifest. Stable plasma protein solutions can withstand pasteurization but labile blood coagulation factors are most often inactivated or significantly reduced in potency during such heating. This restricts practical applications. As a result, recipients of Factor VIII, gamma-globulin, Factor IX, fibrinogen, etc., must often accept the risk that the valuable protein components being administered may be contaminated with hepatitis viruses as well as other infectious viruses. As a result, these recipients face the danger of becoming infected by these viruses and having to endure the damage which the virus causes to organ systems and consequent incapacitation and illness which may lead to death. Therefore, there is a need for a more effective yet practicable method for purification of the heat-sensitive plasma, specifically a method for viral sterilization without the use of heat.

Thus a very special need exists for the development of means and methods for the manufacture and isolation of highly purified Factor IX which can thereafter be formulated into a potent, quick-acting, therapeutic blood product which is stable in vitro and which provides effective relief for patients encountering a critical bleeding incident.

The present invention is directed to achieving three goals, namely, (1) a safe, 2) viral inactivated protein-containing composition, (3) without incurring substantial protein denaturation. These three goals are not necessarily compatible since, for example sterilization inactivates viral infectivity, but substantially denatures the valuable plasma proteins, for example, beta-propiolactone inactivates viral infectivity but is unsafe, and substances such as formaldehyde inactivate viruses, but also substantially denaturate the valuable plasma proteins, for example, Factor IX.

It is therefore desirable to provide a process for obtaining protein-containing compositions which does not substantially denature the valuable protein components therein and which does not entail the use of proven carcinogenic agents (such as B-proprionolactone). More especially, it is desirable to provide blood protein, containing compositions in which substantially all of the hepatitis viruses and other viruses present are inactivated. It is a further object to provide products from cancer or normal cells or from fermentation processes of cells following given insertion of recombinant DNA which are substantially free of virus, including lipid-containing viruses, which comprise a category containing known infective agents of plasma.

SUMMARY OF THE INVENTION

It has now been discovered that when a protein-containing composition, such as whole blood, blood cell proteins, blood plasma, a blood plasma fractionation precipitate, a blood plasma fractionation supernatant, cryoprecipitate, cryosupernatant, or portion or derivative thereof or serum [or a non-blood product produced from normal or cancerous cells (e.g. via recombinant DNA technology)] is contacted with a chemical disinfectant for a sufficient period of time, viruses (such as the hepatitis virus or the human immunodeficiency virus (HIV)) present in a pharmaceutic composition, are virtually entirely inactivated without denaturation of proteins therein. A combination of chemical and physical means applied to a blood protein mixture or concentrate thereof or fraction thereof provides a safe, viral free protein-containing composition without denaturation of the protein.

The present invention provides a highly efficaceous combination of chemical and physical means for rendering a blood product, which contains labile blood proteins and viruses, free of viruses, preferably without incurring protein denaturation. The present invention relates generally to blood component therapy and more particularly to unique means and methods of purifying Factor IX from prothrombin complex concentrates or other sources of Factor IX including culture supernatants containing Factor IX from recombinant DNA technology.

The process comprises the steps of:

(a) mixing the blood product with an effective amount of a chemical disinfectant, preferably a selected chemical disinfectant which does not denature the protein in the blood product, and a buffer;

(b) allowing the mixture to stand for a time sufficient to inactivate substantially all of the viruses;

(c) if desirable, removing the chemical disinfectant; and (d) physically removing the inactivated and active viruses from the blood product.

Preferably, the chemical processing step is carried out on a previously purified blood product. For example, the purification and chemical treatment may comprise the following steps:

(a) chromatographing the blood product on a monoclonal antibody affinity matrix to purify it;

(b) eluting the chromatographed blood product from the monoclonal affinity matrix with a selected chemical disinfectant in buffer or eluting with a non-disinfectant, alternate eluting agent followed by addition of a chemical disinfectant;

(c) allowing the eluted mixture to stand for a time sufficient to inactivate substantially all of the virus;

(d) if desirable, separating the chemical disinfectant from the active blood product by dialysis; and (e) physically removing the inactivated and active viruses from the blood product.

By such procedures there is provided a blood protein-containing composition free of viruses, without protein denaturation. As used herein, blood protein containing compositions include blood cell derivatives (e.g., hemoglobin, alpha-interferon, T-cell growth factor, platelet-derived growth factor, etc.), plasminogen activator, blood plasma, blood plasma fraction, blood plasma precipitate (e.g., cryoprecipitate, ethanol precipitate or polyethylene glycol precipitate), or supernatant (e.g., cryosupernatant, ethanol supernatant or polyethylene glycol supernatant). Blood protein containing compositions are characterized by the presence of one or more labile blood proteins such as Factor IX.

The above methods are particularly useful for pharmaceutical compositions containing vitamin K-dependent proteins, including Factor II, Factor VII, Factor IX, Factor X, prothrombin, Protein C, Protein S and the like, especially a purified Factor IX solution having a high specific activity. The labile blood proteins may also comprise an antibody against infectious hepatitis or an antibody against human immunodeficiency virus.

The process of the present invention surpasses prior processes in providing a combination of high yield of the desired protein with high purity, and particularly with relatively low contamination by other clotting factors. The present invention provides an easy to manage and economical combination of chemical and physical means so as to provide an easy to use final formulation. The present invention also avoids unnecessary and expensive purification manipulations and produces an easy to use final formulation that is substantially free of risk.

DETAILED DESCRIPTION OF THE INVENTION

The present process is directed to the inactivation and removal of viruses in virus-contaminated protein-containing compositions, particularly those that contain blood proteins such as, for example, prothrombin complex (Factors II, VII IX and X) and cryoprecipitate (Factors I and VIII). It is also concerned with sera containing one or more blood proteins, with blood protein-containing fractions containing at least one blood protein such as the Factor II, Factor VII, Factor IX, Factor X, fibrinogen and an Immune Globulin (e.g. IgG, IgM, etc.), and with cell lysates or proteins induced in blood cells. More particularly, it is directed to inactivation and removal of lipid-containing viruses and preferentially inactivation and removal of hepatitis B and non-A, non-B viruses. Other viruses inactivated and removed by the present process include, for example, cytomegaloviruses, Epstein Barr viruses, lactic dehydrogenase viruses, herpes group viruses, rhabdoviruses, leukoviruses, myxoviruses, alphaviruses, arboviruses (group B), paramyxoviruses, arenaviruses, coronariviruses and human immunodeficiency virus (HIV).

The preferred process inactivates and removes viruses of a blood product, which contains labile blood proteins and viruses, without incurring protein denaturation. It comprises the steps of:

(a) chromatographing the blood product on a monoclonal antibody affinity matrix;

(b) eluting the chromatographed blood product from the monoclonal antibody affinity matrix with an effective amount of a selected chemical disinfectant;

(c) allowing the eluted mixture to stand for a period of time and at a particular temperature sufficient to inactivate substantially all of the virus;

(d) if desirable, separating the chemical disinfectant from the active blood product by dialysis; and (e) physically removing the inactivated and active viruses from the blood product.

The chemical disinfectant can be selected from agents known to substantially inactivate lipid-containing viruses, such as organic solvent/detergent combinations, or from a list of agents with less specificity for virus type, such as sodium thiocyanate.

Sodium thiocyanate is the preferred chemical disinfectant for use in the present invention and is employed in an amount between about 0.5M and about 6M, preferably between about 0.5M and about 2M and more preferably between about 1.5M and 2M.

The physical means for removing the inactivated and active viruses from the blood product is selected from the group consisting of ultrafiltration, ultracentrifugation and electrophoresis. The preferred physical means is ultrafiltration.

There are alternate methods for rendering a blood product free of viruses in addition to the preferred method of the invention. The first alternate method uses the chemical means only without utilizing the physical means. Such method comprises contacting the impure blood protein with a chemical disinfectant only. The second alternate method uses the physical means first followed by inactivation with a chemical disinfectant and then optionally using a physical means to remove both inactivated and active viruses.

A third alternate method comprises the steps of:

(a) chromatographing the blood product on a monoclonal antibody affinity matrix to purify it;

(b) eluting the chromatographed blood product from the monoclonal affinity matrix with a selected chemical disinfectant;

(c) omitting further contact with the chemical disinfectant; and (d) separating the inactivated and active viruses by physical means so as to recover the purified, active blood product.

A fourth alternate method comprises the steps of:

(a) chromatographing the blood product on a monoclonal antibody affinity matrix to purify it;

(b) eluting with a non-disinfectant eluting agent followed by addition of a chemical disinfectant;

(c) allowing the eluted mixture to stand for a time sufficient to inactivate substantially all of the virus; and (d) optionally physically removing the inactivated and active viruses from the blood product.

Treatment of blood protein-containing compositions with a chemical disinfectant is carried out at a temperature of about 4 to 25° C., preferably 4° C. Contact of the chemical disinfectant with the blood protein-containing compositions is for about 1 to 2.5 hours, preferably at least 1 hour.

Normally, after the chemical treatment, the chemical disinfectant is removed, although such is not necessary in all instances depending upon the nature of the virus inactivating agents and the intended further processing of the blood plasma protein-containing composition.

In a most preferred embodiment of the present invention, the blood product is purified by chromatographic separation on a monoclonal antibody affinity matrix, then treated with sodium thiocyanate, for a time sufficient to kill the virus, and then ultrafiltered at least once using a membrane having a pore size effective to retain the virus, e.g., an exclusion limit of about 100,000 Daltons, and a pressure sufficient to maintain an adequate flow rate, e.g., about 5 p.s.i.

When the blood product (the example used here is Factor IX) is pre-purified by chromatography on a monoclonal antibody affinity matrix, specific activities as high as 190 units/mg of protein can be obtained. The sodium thiocyanate treatment can be conveniently carried out by using a sodium thiocyanate solution to elute the composition from the matrix and then allowing the mixture to stand for a time sufficient to kill the virus.

Each of these steps, i.e., pre-purification, chemical sterilization, and retentive filtration is very effective in reducing viral infectivity. When used together, a virus-safe ultrafiltrate should be obtained. Substantially incomplete viruses, or viral components may or may not be effectively removed depending on their molecular weight and diameter; however, such incomplete or defective particles would not be expected to be infectious in the host. Additional purification of Factor IX, may be achieved, if desired, by chromatography on amino-hexyl Sepharose.

Of immediate but not exclusive interest is coagulation Factor IX, a pharmaceutical composition useful for the treatment of Hemophilia B. Factor IX, which has a molecular weight of less than 100 K Daltons is a member of the family of vitamin K-dependent coagulation factors, which include Factor II, Factor VII, Factor X, Protein C, Protein S. and the like whose molecular size is in the range of 60–70 K Daltons. Coagulation factors, such as Factor IX, are prepared from human plasma and may be contaminated with a number of potentially infective and dangerous viruses. The virus particles of major concern are hepatitis B virus and HIV, which have diameters of 42 and 100 nanometers (nm), respectively. As will be shown, the diameter of these virus particles is such that ultrafiltration through either a XM300 or XM100 membrane will effectively remove them from a Factor IX coagulation factor or other pharmaceutical products. From present knowledge, it would also be an expected characteristic of hepatitis non-A and non-B virus.

The present process permits the preparation of blood product derivatives such as Factor VIII, gamma globulin, Factor IX or the prothrombin complex (Factors II, VII, IX, X), fibrinogen and any other blood derivatives with characteristics suited to these specifications, all of which contain little or no residual infective hepatitis or other viruses.

By the same manipulative steps discussed above, viruses present in products of normal or cancerous cells can be inactivated while retaining labile protein activity in such products. For instance, by the same chemical inactivation treatment one can inactivate products produced using normal or cancer cells, the exudate from normal or cancerous cells, hybridomas and products produced by gene splicing. Such treatment does not substantially adversely affect the desired protein. Cells used for production of desired protein can, of course, be mammalian as well as non-mammalian cells.

The present invention may be embodied in other specific forms without departing from the spirit or essential attributes thereof.

METHODS FOR ESTIMATING THE EFFICACY OF THE INVENTION

The size of macromolecules including proteins is most often defined and referred to by the weight of the molecule in mass units. A molecule with a weight of 1000 Daltons (1K Dalton) may also be described by the statement that 1 mole of the pure molecule will weigh 1000 grams. (For this application it is more convenient to refer to the physical dimensions of the protein molecules rather than their molecular weight.)

Protein molecules are linear chains of covalently bonded amino acids. In solution, these chains coil and refold in specific ways, and when visualized by appropriate techniques are seen to be compact spheres, ellipsoids, rods or fibers. The science of predicting the shape of individual molecular species is formative, but the shape can be determined by known physical methods. Until a strong deviation is determined by precise measurement and the impact of this accounted for, the practitioner assumes that the shape of the molecule is a sphere. If the molecular size by weight in Daltons is determined by known techniques and if the compactness (density) of the protein folding is available, calculation of the molecular dimensions of a spherical particle can be determined by simple geometry. Based on accumulated measurements it is known that the particle densities of protein molecules vary and can be distinctive for each protein. The variance, however, is not generally great and an average or typical value may be used without great error. This is usually expressed as the partial specific volume ($\bar{v}$) which is the reciprocal of density. A typical specific volume for proteins is 0.75 cc/gm. Thus, for the examples that follow, a protein molecule of molecular weight 100,000 Daltons, using the definition of the unit of Daltons, weighs $10^5$gm per $6.023\times10^{23}$ molecules of the protein. Using the nominal partial specific volume of 0.75 cc/gm, the volume occupied by a single molecule of this protein is $0.1245\times10^{-18}$ cubic centimeters. From the formula for the volume of a sphere, a diameter of 6.2 nanometers (nm) for the protein is calculated. An ultrafiltration membrane with an exclusion limit of 100,000 Daltons should theoretically remove virus particles with diameters in excess of 6.2 nm from a pharmaceutic composition of components less than 100,000 Daltons in molecular weight.

Many experimenters working to elucidate methods for HIV virus reduction have often used (as virus innoculum) the supernatant tissue culture medium from cultured cells known to be infected with virus. These media do not have the same chemical composition as that which is being processed to test virus reduction. Most of the media, in fact, contain as much as 10% of fetal bovine serum as a nutritional growth supplement. When directly used to innoculate the purification/processing system, the investigator is forced to conclude either that (a) any effect of the added tissue culture components is minimized by the use of a small innoculum to process system ratio, say, 1:10 by example, or (b) the effect of the added components can, in any circumstance, be ignored. Either of these conclusions is unacceptable when this approach can be reasonably avoided.

There are further technical (and experimental design) objections to the use of cell culture media as direct sources of infective HIV. Infected tissue culture cells are known (in general) to produce titers of infective virus (in the supernatant growth media) of $10^5$ to $10^8$ $TCID_{50}$ (50% infectious dose in tissue culture assay). Most reports indicate the lower end of this range is more usual than the higher. All assay systems used to detect and measure infective titer will have a lower limit of detection sensitivity. By definition of the TCID assay commonly used for viruses which are not plaque forming, the lowest positive assay is 1 $TCID_{50}$ per volume of assay sample. In the application used, and depending on the volume of test material assayed, the sensitivity of any investigator's assay could vary from less than $10^0$ to $10^2$ $ID_{50}$ per ml of test sample. (Other types of assay systems have been described of HIV. Many published reports show less sensitivity. By comparison to the above, a sensitivity limit equivalent to $10^2$ $ID_{50}$ per ml of assay sample is not uncommon for alternate assay methods).

Consider then, the available limits of demonstration for the effectiveness of viral reduction mechanisms. If the source innoculum were no more than a titer of $10^5$-$10^8$ and the innoculum volume were 1:10 of the test process composition, the initial virus titer for the reduction experiment would be no higher than $10^4$-$10^7$. Depending on the care used in the selection of an assay system, a final virus titer seen as "undetectable" could contain as much as $10^2$ infective virus. Properly expressed (without improper emphasis that the non-detectable was potentially 0) the reduction which can be demonstrated is no more than $10^2$ to $10^5$ $ID_{50}$.

Herein, a different course of design and action has been chosen to demonstrate that the present virus reduction is far more potent than those demonstrated by others. It was originally estimated (Petricciani J. C., et al.: Case for concluding that heat treated, licensed, antihemophilic factor is free from HTLV-III, Lancet II: 890-891, 1985) (Note: HTLV III=HIV-1) that a safety margin for the preparation of blood products could be measured against the concept of a "worst case" scenario In the worse case, clotting factor concentrates could have viral titers of $2\times10^5$ (approximately 5.5 $\log_{10}$) if no viral reduction treatment was employed. Statistical treatment of this estimate would suggest a much higher safety limit is needed if the patient is to receive $2\times10^5$ doses, or nearly so, in a lifetime since clotting factors are chronic use drugs. Thus, as one group of examples, the reductions cited for model virus studies as described in U.S. Pat. No. 4,764,369 to Neurath, et al., U.S. Pat. No. 4,540,573 to Neurath, et al. and U.S. Pat. No. 4,820,805 to Neurath, et al., the disclosures of which are incorporated by reference, (all of which are marginally demonstrative of the desired safety margin cited by Petricciani, et al.) are insufficient to demonstrate the higher safety margin necessitated by chronic use. In our case, the HIV virus is partially purified and concentrated by ultracentrifugation to be substantially free of tissue culture media components. The virus is suspended in a buffer composition selected to be compatible with the processing fluids under study. There is no chemical perturbation (other than virus) which would render the present experiments suspect for comparison to the practiced art of the process. A concentrate titer of $10^{10}$-$10^{12}$ $ID_{50}$ per ml is obtained. This art is readily applied to other viruses such as those described in U.S. Pat. No. 4,764,369 to Neurath, et al., U.S. Pat. No. 4,540,573 to Neurath, et al. and U.S. Pat. No. 4,820,805 to Neurath, et al.

This careful antecedent to the experimental design still presents experimental limitations. If any step in a multi-step virus reduction process is so remarkably effective as to reduce the virus titers to this much higher limit (even with an assay system that is sensitive to less than $10^{)}$), the total effectiveness of the multi-step system cannot be studied in a single experiment. Ideally, for the best scientific design, the initial titer measured prior to conducting a single processing step should be high enough that residual virus is present after the processing step. Thus, a well defined increment of reduction can be stipulated. If the residual titer is insufficient to challenge a subsequent step and again assure residual virus at the end of that step, a defined limit for the second step cannot be stipulated. In this combined process, each of the two processing steps provides reduction of titer essentially equivalent to the maximum that can be reasonably achieved, even with the added caution of using an extraordinarily enriched virus concentrate. In our HIV experiments, the initial titers used for our laboratory demonstration of virus reduction potential, are many $\log_{10}$ in excess of what could be expected from the accidental contamination of the protein compositions during actual practice of preparing therapeutic preparations. (C. F. Petricciani, et al.) This demonstrates a wide margin of safety in the practice of this invention and allows for the extra margin of safety required by statistical analysis of chronic drug use.

Thus the combined numerical reduction of two sequential reduction steps when each, independently, is at the limit of our ability to measure effectiveness, cannot be specified, but the applied redundancy of virus reduction mechanisms of high efficacy can be predicted. In other arts, such as electronics, the concept of redundancy is used to increase levels of assurance of fail-safe operation during use. This concept has not been previously recognized for the assurance of safety from virus transmission in plasma protein therapeutics.

EXAMPLE 1

Removal of Virus by Ultrafiltration

A purified Factor IX was obtained from PROTHAR® by chromatography on a monoclonal antibody affinity matrix specific to Factor IX. It contained approximately 0.065 milligrams of protein and 8 units of Factor IX activity per milliliter of solution. The purified preparation was ultrafiltered using an Amicon XM300 membrane and pressure of 5 p.s.i. The ultrafiltration proceeded very rapidly (about 2.5 ml/min). The filtrate was subsequently re-filtered through an Amicon XM100 membrane. The Factor IX activity in the final ultrafiltrate was 67%. Losses were not the result of Factor IX inactivation since specific activity was unaltered.

EXAMPLE 2

Part A - Preparation of A Virus Stock

A virus stock concentrate was prepared by infecting (CEM) cells at a multiplicity of infection of approximately 1. The cultures were established in 490 $cm^2$ Corning roller bottles containing approximately 450 ml of RPMI 1640 medium sufficient as is supplemented with 10% fetal bovine serum, penicillin, streptomycin, and 0.002 mg/ml polybrene. The maximum cell density achieved in the cultures after four days of infection was $1\times10^6$ cells/ml, at which time the cultures were diluted by half with fresh medium. The total volume of the cultures was 1800 ml. Incubation was continued for three more days when extensive cytopathology was observed. The cultures were filtered through a 1.2 uM cellulose acetate filter. Virus was pelleted from the filtrate by centrifugation at 61,000×g for 4 hours at 4° C. The pelleted virus was resuspended with PBS (phosphate buffered saline solution). The stock contained more than 10 $\log_{10}$ $ID_{50}$ per ml.

Part C - Inactivation of Virus by NaSCN Treatment

Factor IX was eluted from a monoclonal antibody affinity matrix with 3M NaSCN and subsequently desalted with Sephadex $G_{10}$. One milliliter of the above HIV stock was mixed with 20 ml of Factor IX solution, and 2 ml of the resulting mixture was added to varying amounts of 6M sodium thiocyanate (NaSCN) and buffer (0.01 M TRIS-HCL and 0.02 M EDTA, pH 8.0), as shown in Table II, to achieve the appropriate NaSCN concentration:

TABLE II

| SAMPLE | 6M NaSCN | BUFFER | FINAL NaSCN CONCENTRATION |
|---|---|---|---|
| A | 1.00 ml | 1.00 ml | 1.5 |
| B | 1.35 ml | 0.65 ml | 2.0 |
| C | 2.00 ml | 0.00 ml | 3.0 |
| D | 1.35 ml | 0.65 ml | 2.0 |

Samples A, B and C were allowed to stand for 1 hour at 4° C. and sample D was allowed to stand for 1 hour at 25° C. Each sample was then centrifuged at 105,000×g for 90 minutes. The pellets were resuspended in 1 ml PBS and assayed for HIV by direct observation of the cytopathic effects of the virus on CEM cells. The assay method used in this example inherently rounds off titer to the nearest 0.5 log increment. The results are shown in Table III.

TABLE III

| SAMPLE | TOTAL $LOG_{10}$ $ID_{50}$ (found) | $LOG_{10}$ REDUCTION (due to treatment) |
|---|---|---|
| A | 1.0 | 8.0 |
| B | 1.0 | 8.0 |
| C | 1.0 | 8.0 |
| D | 1.0 | 8.0 |

(Initial virus titer for each sample, prior to treatment was 9 $\log_{10}$).

The results show that the sodium thiocyanate treatment inactivated 8 logs of HIV. They further show that concentrations of above 1.5 were not more effective, that the use of a buffer was not required (see Sample C), and that treatment at both 4° and 25° C. was effective.

EXAMPLE 3

Part A - Preparation of A Virus Stock

A virus stock concentrate was prepared by infecting (CEM) cells at a multiplicity of infection of approximately 1. The cultures were established in 490 $cm^2$ Corning roller bottles containing approximately 450 ml of RPMI 1640 medium sufficient as is supplemented with 10% fetal bovine serum, penicillin, streptomycin, and 0.002 mg/ml polybrene. The maximum cell density achieved in the cultures after four days of infection was $1\times10^6$ cells/ml, at which time the cultures were diluted by half with fresh medium. The total volume of the cultures was 1800 ml. Incubation was continued for three more days when extensive cytopathology was observed. The cultures were filtered through a 1.2 uM cellulose acetate filter. Virus was pelleted from the filtrate by centrifugation at 61,000×g for 4 hours at 4° C. The pelleted virus was resuspended with PBS (phosphate buffered saline solution). The stock contained more than 11 $\log_{10}$ $ID_{50}$ per ml.

Part B - Removal of Virus by Ultrafiltration

Five milliliters of HIV stock (HIV =Human Immunodeficiency Virus, LAV- I Strain) were added to 45 ml of affinity purified and Sephadex $G_{10}$- desalted Factor IX solution. The mixture was poured into an Amicon stirred celled (180 ml capacity) outfitted with a XM100 membrane (6.2 nm pore diameter) and ultrafiltered nearly to dryness. The unit was subsequently washed three times with 0.05 M sodium chloride (NaCl), 0.005 M histidine, pH 7.0, yielding a total of 12 ml. of wash. The starting material, the Factor IX-containing ultrafiltrate, and the residual wash were assayed for HIV.

The results in Table I show that ultrafiltration of a mixture containing 11.7 logs of HIV virus resulted in a Factor IX-containing ultrafiltrate where HIV infectivity was reduced to 0.5 log, a reduction of 11.2 logs.

TABLE I

| SAMPLE | TOTAL $LOG_{10}$ $ID_{50}$ | $LOG_{10}$ REDUCTION |
|---|---|---|
| Starting Material (HIV virus prior to ultrafiltration) | 11.7 | — |
| Residual Wash | 10.1 | 1.6 |
| Ultrafiltrate | 0.5 | 11.2 |

EXAMPLE 4

Removal of Virus by Ultrafiltration from Unpurified Factor IX Composition

This example shows that pressure ultrafiltration of reconstituted PROTHAR® yielded an ultrafiltrate of low activity. The product covered by this registered trademark of Armour Pharmaceutical is a stable lyophilized concentrate of human Factors II, VII, IX and X. It is prepared from pooled human plasma. Upon reconstitution it is a concentrated protein solution containing approximately 18 milligrams of total protein and 33 units of Factor IX activity per milliliter. The specific activity of Factor IX in the product ranges from 0 8–2.0 units per milligram of total protein.

Part A - Membrane With Cut-Off of 100 K Daltons

In the first run, PROTHAR® was diluted 1:1 with 0.05M Tris-HCL, pH8.0. The resultant solution was ultrafiltered through an Amicon XM100 membrane (molecular weight cut-off of 100 K Daltons) using a pressure of 15 p.s.i. The ultrafiltration proceeded very slowly (about 0.25 ml/min), and the flow rate slowed as the protein inside the stirred cell became more concentrated. Only about 1% of the Factor IX activity found in the starting material appeared in the ultrafiltrate. Repetition of this experiment with a 1:6 initial dilution of the reconstituted PROTHAR® and pressure of 5 p.s.i. gave an ultrafiltrate with a similar low Factor IX activity. Factor IX activity, in this and all other instances, is assayed by determining the degree of correction in APTT time of Factor IX - deficient plasma. J. H. Lenahan, Phillips and Phillips, Clin. Chem., Vol. 12, page 269 (1966).

The results show that although Factor IX has a molecular weight of only 60–70 K Daltons, it did not ultrafilter to a significant extent through a membrane whose porosity should have allowed its passage into the ultrafiltrate A reasonable explanation is based on the phenomenon known as membrane polarization. Protein rejected (retained) by the membrane, if not immediately mixed back into the main body of the solution being filtered, is concentrated into a thin solution layer at the membrane surface. The layer may become so concentrated that it become "gelatinous" and constitutes a new form of membrane overlying that in use. The properties of this protein membrane are generally highly distinct from those of a mechanical membrane with a much lower porosity.

Part B - Membrane With Cut-Off of 300 K Daltons

Subsequent experiments were performed using an Amicon XM300 membrane (molecular weight cut-off of 300 K Daltons), pressures of 5 p.s.i., and reconstituted PROTHAR® dilutions of 1:6 and 1:10. Only about 17–19% of the Factor IX activity was found in the ultrafiltrate. The addition to the solution to be ultrafiltered of 0.1% Tween 80 (a surfactant) did not improve the results. In all instances, the ultrafiltered Factor IX showed only a 6 to 8-fold purification over the starting material.

The results show that the separation was only moderately successful with the more porous membrane.

The results show that while ultrafiltration can be successfully used to further treat an affinity-purified Factor IX solution, it is not equally practical in obtaining a high Yield of Factor IX from less pure starting material.

EXAMPLE 5

Alternative Chemical Disinfectants and Monoclonal Antibody Purification

A Factor IX concentrate solution containing about 1–3 units of Factor IX per mg of protein is initially contacted with Sindbis virus to a final titer of 8–9 $log_{10}$ $TCID_{50}$ and thereafter brought into contact with 0.1% tri(n-butyl)phosphate and 1% Tween 80 (detergent) as described in U.S. Pat. No. 4,764,369 to Neurath, et al., the disclosure of which is incorporated by reference. It is expected that Sindbis virus infectivity will be reduced by more than 4 $log_{10}$ of virus and that active Factor IX content will be in excess of 80% of the initial value.

This solvent/detergent treated Factor IX solution is contacted with a monoclonal antibody as described in U.S. Pat. No. 4,786,726 to Smith, the disclosure of which is hereby incorporated by reference. It is expected that a purified solution of Factor IX will be obtained. It is further expected that this solution will be further depleted of infectious Sindbis virus by reason of the purification obtained, and that the titer of virus will be undetectable.

The Factor IX solution obtained is further contacted with HIV virus to obtain a final titer of 8–9 $log_{10}$ of virus. The protein content is adjusted to about 0.025 to 0.065 mg of protein per milliliter. The resulting solution is filtered through a membrane with an effective porosity equivalent to 100 KD molecular weight cut-off. It is expected that from 80–100% of the F.IX will be recovered and that HIV virus titer will be reduced to an undetectable level.

The Factor IX solution is concentrated to a potency of about 100 International units per ml and dialyzed against a buffer consisting of 0.066 M sodium chloride (NaCl), 0.01 M histidine, 3% mannitol, pH 7.0±0.2. When performed without the addition of exogenous test virus, this material is sterile filtered (0.1 micron filter) and lyophilized to obtain a product suitable for pharmaceutic use.

EXAMPLE 6

Alternate Means of Applying Chemical Disinfectant

A Factor IX concentrate solution containing about 1–3 units of Factor IX per mg of protein is contacted with the monoclonal antibody described in U.S. Pat. No. 4,786,726 to Smith. Purified Factor IX is eluted from the monoclonal antibody with a chaotropic agent such as EDTA (ethylenediaminetetracetic acid). It is expected that the Factor IX solution obtained will contain purified Factor IX of high specific activity and that the yield will be 80–100%.

The Factor IX solution obtained is further contacted with HIV virus to obtain a final titer of 8–9 $log_{10}$ of virus. Sodium thiocyanate is added to the Factor IX-HIV mixture so that the final concentration of NaSCN is about 1.5 M and the Factor IX-HIV mixture is allowed to stand at a temperature of between 4° C. and 25° C. for a period of time from 1 to 2.5 hours. It is expected that Factor IX potency will not be affected by the disinfectant treatment and that the titer of HIV infectivity will be reduced to undetectable levels.

The solution is then dialyzed to remove the chemical disinfectant and then filtered through a membrane with an effective porosity equivalent to 100 KD molecular weight cut off. It is expected that 80–100% of the Factor IX activity will be recovered and that the HIV titer will be further reduced It is also expected that incomplete or altered viral particles will be removed from the Factor IX solution by the filtration.

The Factor IX solution is concentrated to a potency of about 100 International Units per ml and dialyzed against a buffer consisting of 0.066 M sodium chloride (NaCl), 0.01 M histidine, 3% mannitol, pH 7.0±0.2. When performed without the addition of exogenous test virus, this solution is sterile filtered (0.1 micron filter) and lyophilized to obtain a product suitable for pharmaceutical use.

While specific embodiments of the invention have been shown and described, it should be apparent that many modifications can be made thereto without departing from the spirit and scope of the invention. Accordingly, the invention is not limited by the foregoing description.

What is claimed is:

1. A redundant process for rendering a blood product selected from the group consisting of prothrombin, Factor II, Factor VII, Factor IX, Factor X, Protein C and Protein S containing labile blood proteins and HIV viruses, free of active HIV viruses, which comprises:

(a) chromatographing said blood product on a monoclonal antibody affinity matrix to purify it;

(b) eluting the chromatographed blood product from the monoclonal antibody affinity matrix with an effective amount of sodium thiocyanate which does not denature said blood product;

(c) allowing the eluted mixture to sand for a period of time and at a temperature sufficient to inactivate substantially all of said HIV viruses;

(d) dialyzing said eluted mixture to remove said sodium thiocyanate; and (e) removing said inactivated and residual active HIV viruses from said eluted mixture.

2. A process for rendering a blood product selected from the group consisting of prothrombin, Factor II, Factor VII, Factor IX, Factor X, Protein C and Protein S containing labile blood proteins and HIV viruses, free of active HIV viruses which comprises, contacting said blood product with a buffer and an effective amount of sodium thiocyanate which does not denature said blood product for a period of time sufficient to inactivate substantially all of the HIV viruses.

3. The process of claim 2 wherein after the blood product and sodium thiocyanate mixture has been allowed to stand for a period of time sufficient to inactivate substantially all of the HIV viruses, the HIV virus is removed.

4. The process of claim 2 wherein after the blood product and sodium thiocyanate mixture has been allowed to sand for a period of time sufficient to inactivate substantially all of the HIV viruses, the sodium thiocyanate is removed.

5. The process of claim 2 wherein the amount of sodium thiocyanate mixed with the blood product is in an amount from about 0.5M to about 6M.

6. The process of claim 2 wherein the amount of sodium thiocyanate mixed with the blood product is in an amount from about 0.5M to about 2M.

7. The process of claim 2 wherein the amount of sodium thiocyanate mixed with the blood product is in an amount from about 1.5M to about 2M.

8. The process of claim 1 wherein sodium thiocyanate is in the amount from about 0.5M to about 6M.

9. The process of claim 1 wherein sodium thiocyanate is in the amount from about 0.5M to about 2M.

10. The process of claim 1 wherein sodium thiocyanate is in the amount from about 1.5M to about 2M.

11. A process according to claim 1 or 3 wherein said removing of HIV viruses is by the means of ultrafiltration, ultracentrifugation or electrophoresis.

* * * * *